Dec. 14, 1948. O. F. JONES ET AL Plant Pat. 814

PEACH TREE

Filed Feb. 6, 1947 2 Sheets-Sheet 1

INVENTORS
OSCAR F. JONES
WILBUR C. JONES
BY Bernard Z. Lanzy
ATTORNEY

INVENTORS

OSCAR F. JONES

WILBUR C. JONES

BY

Bernard J. Garvey

ATTORNEY

Patented Dec. 14, 1948

Plant Pat. 814

UNITED STATES PATENT OFFICE

814

PEACH TREE

Oscar F. Jones, Crozet, Va., and Wilbur C. Jones, Hagerstown, Md.

Application February 6, 1947, Serial No. 726,894

1 Claim. (Cl. 47—62)

This discovery relates to improvements in peach trees and the fruit of the same.

*Origin*—This improved peach originated as a chance seedling discovered in an apple orchard in the Crozet district, a commercial peach growing section in the State of Virginia, where the Elberta variety of peach is grown almost exclusively. The seedling first attracted attention because of its rapid growth and deep green foliage, and then later by the hardiness of the bud and blossom and the hereafter mentioned characteristics of the fruit which indicated that it was a new variety.

The discovery was in the summer of the year 1936. The tree had evidently sprouted from a seed that had germinated in the loosened soil from which a defective apple tree had been removed the previous year. As the only peach trees in the vicinity were the Elberta and Georgia Belle varieties, it is presumed that the tree is a cross of these two varieties.

From the parent seedling there have been asexually reproduced a number of other trees and there are now in bearing about seventy-five of these additional trees. All the additional trees so propagated have held true to all the characteristics of the parent tree and fruit and proven the permanency thereof.

During the harvest season of 1946, the parent tree, now ten years of age, had fifteen bushels of fruit on it. Four and one-half measured bushels of fruit were picked from an asexually reproduced tree five years from the date of the bud. Perfect fruit has been harvested from trees asexually reproduced two years from the bud.

In comparison with the Elberta, the tree of this discovery is of more rapid and vigorous growth; the branches are characterized by great flexibility and tensile strength; the tree, under cropping conditions appearing to weep as the heavily laden branches bend gracefully, with a minimum of breakage. Also as compared to the Elberta variety, the discovered tree has been estimated to carry and mature a load of fruit in an amount twenty per cent greater than would be practical on an Elberta tree of similar size, since less pruning is required.

The improved peach has little, if any, resemblance to the Elberta, being a perfect free stone, large (from 2¾ x 3 inches to 3 x 3½ inches), elongated, ovate-oval with a very prominent tip, uniform in size, with the flesh being of fine grain and of rich yellow color with some red splashing towards the stone. The bud and blossom are more resistant to frost and freezes than the Elberta, although resembling the latter in color, in conformation, but being somewhat deeper in shade.

In the accompanying illustration,

Figure 1:
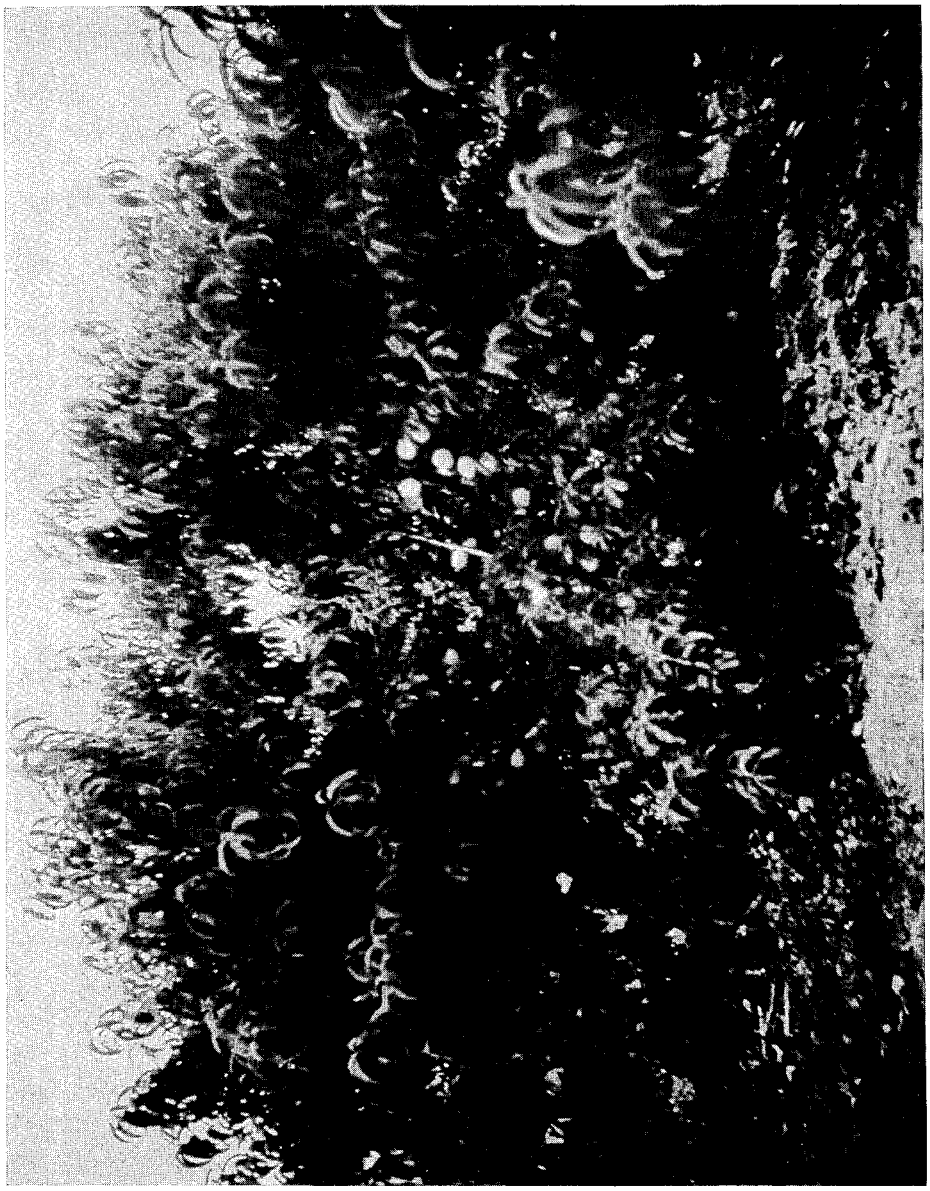
Figure 1 shows an average specimen of the tree of this new variety.
Figure 2:
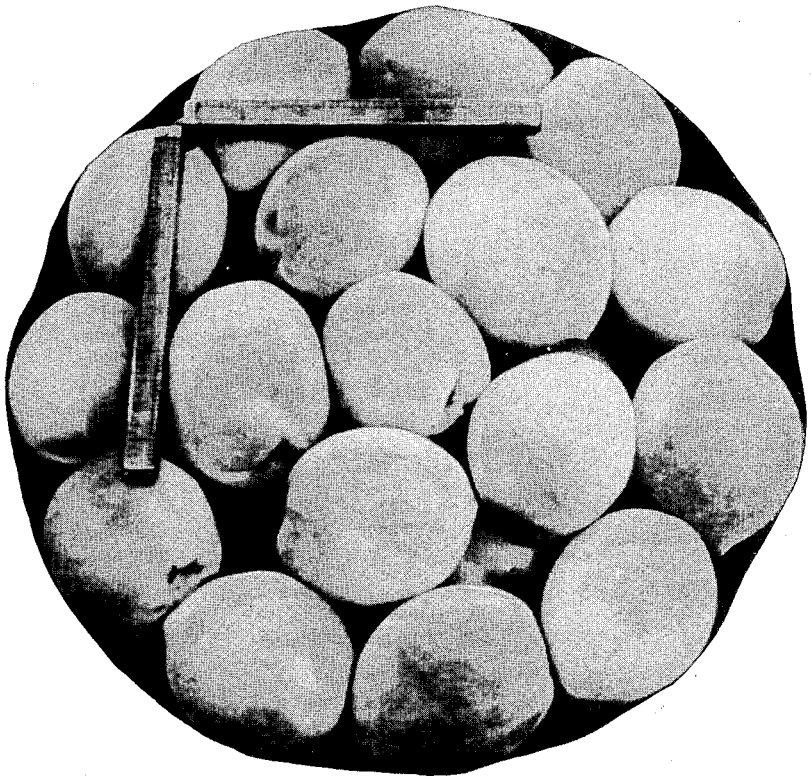
Figure 2 shows specimens of the fruit of this new variety, ripe and ready to eat or ship, and illustrating the uniformity of size which characterizes this new variety of peach.

The following is a detailed description of this new variety of tree and the fruit of the same:

Tree: Large to medium. Vigorous and rapid growth. Spreading and under cropping conditions appears to weep. Dense; hardy. Very productive, bearing at an early age and carrying and maturing a load of fruit that commercial growers have estimated to be 20% greater than would be practical on an Elberta tree of similar size, since less pruning is required.

*Trunk.*—Slender to medium. The wood is tough and not brash and has great flexibility. The bark resembles the Elberta.

*Branches.* — Slender to medium. Rapid growth. The wood is tough and not brash and has great flexibility and tensile strength. Requires less pruning than the Elberta. When heavily laden, branches bend gracefully with a minimum of breakage.

*Leaves.*—The foliage as compared to the Elberta is darker and larger. The leaves are rich dark green and average one inch longer and one-eighth inch wider than the Elberta. Also the leaves are wavy to slightly crinkled with the edge coarsely serrated to almost smooth; obovate-lanceolate; base angle wide; glands reniform, 2–4 in number, inconspicuous, reddish brown.

*Flower-buds.*—The bud and blossom are more resistant to frost and freezes than the Elberta, the blossoms resembling the Elberta in color and conformation but are somewhat deeper in shade.

Fruit: Large (from 2¾ x 3 inches to 3 x 3½ inches), elongated, ovate-oval with a very prominent tip. Color yellow with blush and mottling of red color; quite attractive. Suture striped with russet raised and slightly prominent. Cavity, narrow, deep, acute. Stem end narrow with slight ridging. Stem end and suture firm (the entire fruit ripening evenly). Fruit throughout the tree is quite uniformly large, even though pruning and fruit thinning were light. The fruit ripens in the Elberta season but will remain on the tree at a maturer stage for a longer period than will the Elberta.

*Size.*—Uniform. Larger than the Elberta and varies very little, irrespective of heavy cropping.

*Form.* — Globular, somewhat elongated, ovate-oval with a very prominent tip.

*Skin.*—Color—brilliant cardinal red almost completely covering a golden yellow ground color, even when growing in shade in the interior of the tree. Has only a slight fuzz.

*Flesh.*—Fine grain and rich yellow with some red splashing towards the stone. Flavor—superior and rated as excellent by commercial growers, being distinctly aromatic and pleasing. Quality—best. Stone—free, somewhat flat, roughly corrugated concentrically from the base, with base very narrow and tip sharply pointed. Size—smaller than that of the Elberta. Tendency to split—does not develop an inclination to split, thus eliminating the possibility of the bitter flavor frequently found in the Elberta peach.

Use: Market, local, dessert, culinary, canning.

Keeping quality: Excellent.

Resistance to: Brown rot—excellent. Experiments indicate that when any breakdown of cellular structure takes place, it is not usually in the form of a rot, but rather a gradual loss of moisture followed by shriveling.

Shipping quality: Ships well. Bushel baskets of the fruit have been shipped by express, uniced, to various States and have arrived in perfect condition. Baskets of the fruit have been shipped parcel post to various States and have been delivered in perfect condition.

It is to be understood that the foregoing characteristics are typical, but subject, perhaps, to slight variations which may arise by reason of change of environment.

What we claim is:

A new and distinct variety of peach tree substantially as herein disclosed, characterized by rapid growth, early maturity for production of fruit and flexibility and tensile strength of its branches; and the fruit of such tree characterized by uniformity of size, being elongated, ovate-oval with very prominent tip, development of color when grown in shade, resistance to brown rot, almost entire absence of fuzz, and superior flavor and shipping qualities; and the hardiness of bud and blossom to frost and freezes.

OSCAR F. JONES.
WILBUR C. JONES.

No references cited.